United States Patent [19]

Tsushima et al.

[11] Patent Number: 4,981,860
[45] Date of Patent: Jan. 1, 1991

[54] PYRIDINIUM NITRATE, COMPOSITION CONTAINING SAME AND THEIR USE FOR INHIBITING PLATELET ACTIVATING FACTOR

[75] Inventors: Susumu Tsushima, Highland Park, Ill.; Muneo Takatani; Kohei Nishikawa, both of Kyoto, Japan

[73] Assignee: Takeda Chemical Industries, Ltd., Osaka, Japan

[21] Appl. No.: 470,244

[22] Filed: Jan. 25, 1990

[30] Foreign Application Priority Data

Jan. 30, 1989 [JP] Japan .................. 1-21919

[51] Int. Cl.$^5$ .................. C07D 217/00; A61K 31/47
[52] U.S. Cl. .................. 514/307; 546/147
[58] Field of Search .................. 546/147; 514/307

[56] References Cited

FOREIGN PATENT DOCUMENTS 0147768 7/1985 European Pat. Off. ............ 514/355

OTHER PUBLICATIONS

Tsushima et al., Chem. Abstracts, vol. III(15), Abst. No. 111: 133922-g, Oct. 9, 1989.

*Primary Examiner*—Alan L. Rotman
*Attorney, Agent, or Firm*—Wegner, Cantor, Mueller & Player

[57] ABSTRACT

Novel compound of the formula:

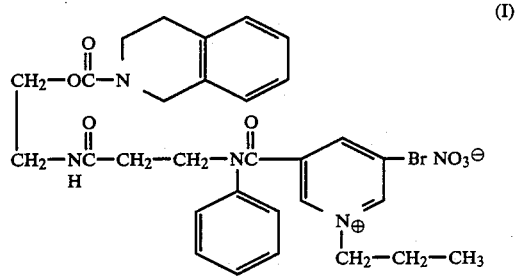

is useful as a platelet activating factor antagonist and is so stable that it is advantageously used as drugs.

3 Claims, No Drawings

PYRIDINIUM NITRATE, COMPOSITION CONTAINING SAME AND THEIR USE FOR INHIBITING PLATELET ACTIVATING FACTOR

BACKGROUND OF THE INVENTION

This invention relates to pyridinium derivatives which are useful as drugs. In more detail, this invention relates to the compound (3-bromo-5-[N-phenyl-N-[2-[[2-(1,2,3,4-tetrahydro-2-isoquinolylcarbonyloxy)ethyl]carbamoyl]ethyl]carbamoyl]-1-propylpyridinium nitrate) of the formula:

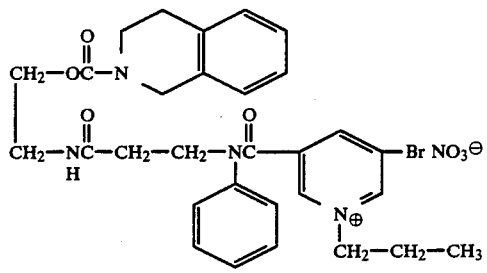
(I)

which is useful as a platelet activating factor (PAF) antagonist.

PAF is a phospholipid which is a chemical mediator present in the body. It has been clarified that PAF plays an important role in allergy, anaphylaxis, and inflammation in vivo, having powerful hypotensive action and platelet agglutinating activity. PAF, when given to an animal, can cause shock resulting in death. Shock symptoms caused by PAF are very similar to those caused by endotoxin, and PAF is known to take part in endotoxin-shock.

Although various compounds have been shown to be PAF-antagonistic, only a few of them are useful PAF antagonists in vivo. Moreover most of the useful PAF antagonists in vivo are restricted in their dosing or have problems in their stability as drugs.

DETAILED DESCRIPTION

This invention offers pyridinium nitrate [Compound (1)] having the formula (I) shown above.

The pyridinium nitrate of this invention can be synthesized by, for example, the methods described in the following.

(A) The compound of the formula:

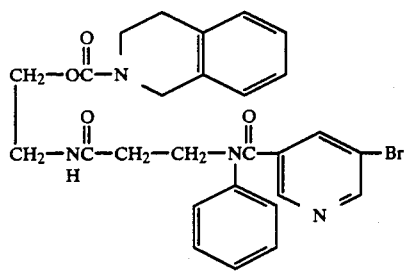
(II)

is allowed to react with the compound represented by the formula:

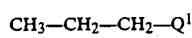  CH$_3$—CH$_2$—CH$_2$—Q$^1$ (III)

wherein Q$^1$ represents a group which substitutes readily at the nitrogen atom (e.g. halogeno such as chloro, bromo, iodo, etc., toluenesulfonyloxy, methanesulfonyloxy, etc.), and an NO$_3^-$ ion is introduced, for example, with ion exchange resin.

(B) The compound represented by the formula:

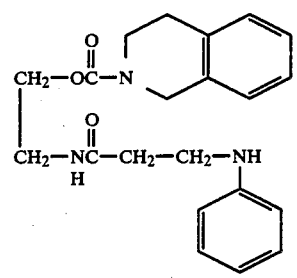
(IV)

and the compound represented by the formula:

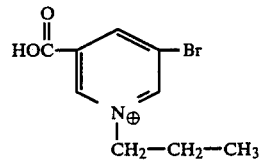
(V)

are subjected to dehydrative condensation.

(C) The compound represented by the formula:

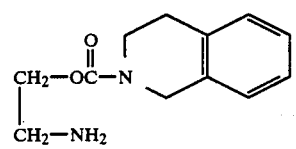
(VI)

and the compound represented by the formula:

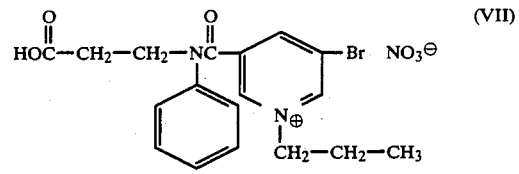
(VII)

are subjected to dehydrative condensation.

(D) The compound represented by the formula:

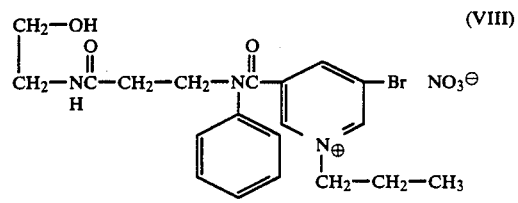
(VIII)

is allowed to react with the compound represented by the formula

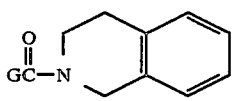
(IX)

wherein G is a halogeno group such as chloro, or phenoxy.

(E) The compound represented by the formula:

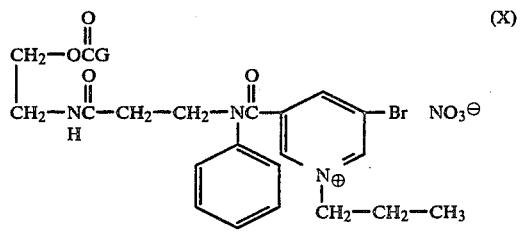
(X)

wherein G is a halogeno group such as chloro, or phenoxy, is allowed to react with the compound represented by the formula:

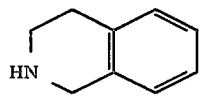
(XI)

The reaction between the compound (II) and the compound (III) in Method A can be performed by using an equivalent or a large excess of the compound (III) for the amount of the compound (II) at 0° C. to +200° C. in the presence or the absence of a solvent. As the solvent, mention is made of toluene, benzene, ether, dioxane, tetrahydrofuran, etc. and the compound (III) itself. The reaction with heating may be allowed to proceed in a sealed tube.

Dehydrative condensation between the compounds (IV) and (V) in Method B and between the compounds (VI) and (VII) in Method C can be conducted for example by a conventional amido-linkage forming reaction. Namely, the reaction can be conducted by using an amido-forming reagent alone, such as 1-ethoxycarbonyl-2-ethoxy-1,2-dihydroquinoline, dicyclohexylcarbodiimide, 1-cyclohexyl-3-(2-morpholynoethyl)carbodiimide meso-p-toluenesulfonate, N,N'-carboxyldiimidazole, diphenyl phosphoric acid, diethyl cyanophosphate, or 1-ethyl-3-(3-diethylaminopropyl)carbodiimide hydrochloride; or by allowing the compound (V) or (VII) to condense with a phenol such as 2,4,5-trichlorophenol, pentachlorophenol, pentafluorophenol, 2-nitrophenol, or 4-nitrophenol, or with an N-hydroxy compound such as N-hydroxysuccinimide, 1-hydroxybenztriazole, N-hydroxypiperidine, N-hydroxy-5-norbornene-2,3-dicarbodiimide, in the presence of a catalyst such as dicyclohexylcarbodiimide, to convert to an active ester, which is then allowed to react with the compound (IV) or (VI); or by allowing the compound (V) or (VII) to react with an acid chloride such as ethyl chlorocarbonate, isobutyl chlorocarbonate, or benzyl chlorocarbonate, to convert to a mixed acid anhydride, which is then allowed to react with the compound (IV) or (VI). The compound (V) or (VII) may be activated into an acid halide by the reaction with phosphorus oxychloride, phosphorus pentachloride, thionyl chloride, or thionyl bromide. The amido-linkage forming reaction can be accelerated desirably by addition of an organic base such as a tertiary amine (e.g. triethylamine, pyridine, dimethylpyridine, N-methylpiperidine), whether it is performed by allowing the compound (V) or (VII) without treatment, or after converting into its active ester, acid halide or mixed acid anhydride, to react with the compound (IV) or (VI). The reaction is performed at −30° to +50° C. in the presence of a solvent (e.g. ether, toluene, benzene, chloroform, dichloromethane, dioxane, tetrahydrofuran), or without solvent.

The reaction between the compound (VIII) and (IX) and the reaction between the compounds (X) and (XI) in Method D and in Method E, respectively, are performed without solvent or in the presence of a solvent (e.g. ether, toluene, benzene, chloroform, dichloromethane, dioxane, tetrahydrofuran, dimethylformamide) at −10° to 150° C. For acceleration of the reaction, a tertiary amine (e.g. triethylamine, pyridine, dimethylaminopyridine, N-methylpiperidine) may be added.

The compound (II) can be produced for example by (i) dehydrative condensation between the compound (IV) and the compound represented by the formula:

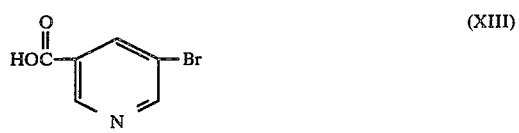
(XIII)

(ii) dehydrative condensation between the compound (VI) and the compound represented by the formula:

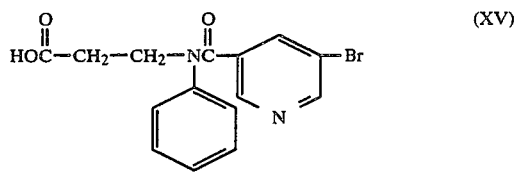
(XV)

(iii) the reaction between the compound represented by the formula:

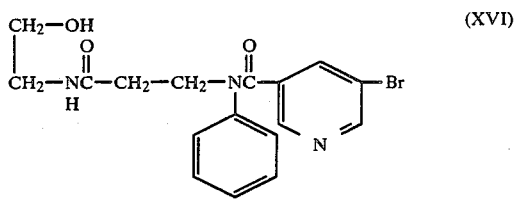
(XVI)

and the compound (Ix), or (iv) the reaction between the compound represented by the formula:

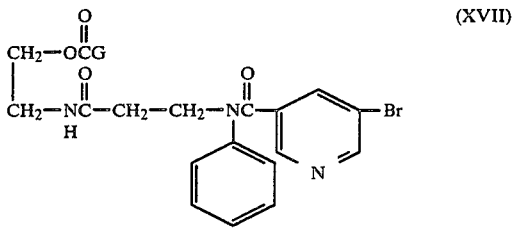
(XVII)

wherein G is the same as described above, and the compound (XI).

The reaction between the compounds (IV) and (XIII) and the reaction between the compounds (VI) and (XV) are performed similarly to the reaction between the compounds (IV) and (V). The reaction between the compounds (XVI) and (IX) and the reaction between the compounds (XVII) and (XI) are performed similarly to the reaction between the compound (VIII) and IX).

The compound (VI) can be obtained for example as follows:

(i)
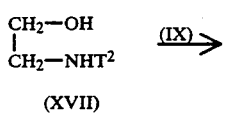
(XVII)

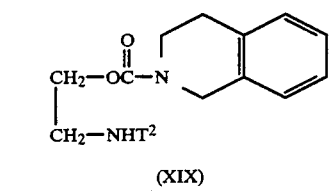
(XIX)

(ii)
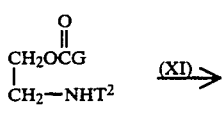
(XX)

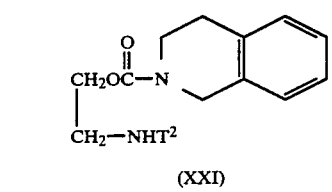
(XXI)

wherein, $T^2$ is a protective group (e.g. an amino-protective group such as benzyloxycarbonyl, tert-butyloxycarbonyl, trifluoroacetyl, trityl, or benzyl), and G is a halogeno group such as chloro or bromo, or a phenoxy.

The reaction between (XVIII) and (IX) and the reaction between (XX) and (XI) are performed under a similar condition as that for the reaction between (VIII) and (IX) in Method D described above.

The compound (IV) can be obtained for example by the following method.

(i)
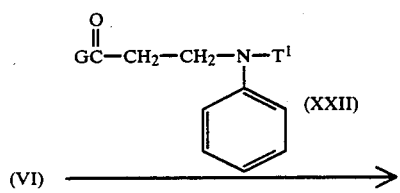
(XXII)

(VI) ⟶

-continued

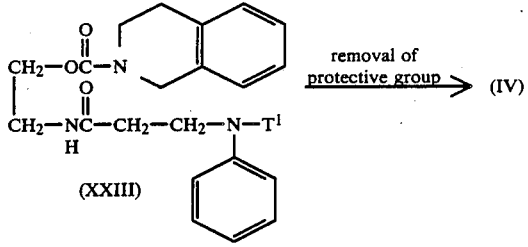
(XXIII)

wherein $T^1$ is a protective group (an amino-protective group such as benzyloxycarbonyl, tert-butyloxycarbonyl, trifluoroacetyl, trityl, or benzyl), and G is the same as described above.

The reaction between (VI) and (XXII) is performed under the same condition as that for the reaction between (VIII) and (IX) in Method D described above.

The compounds (VIII) and (XVI) can be obtained for example by the following method.

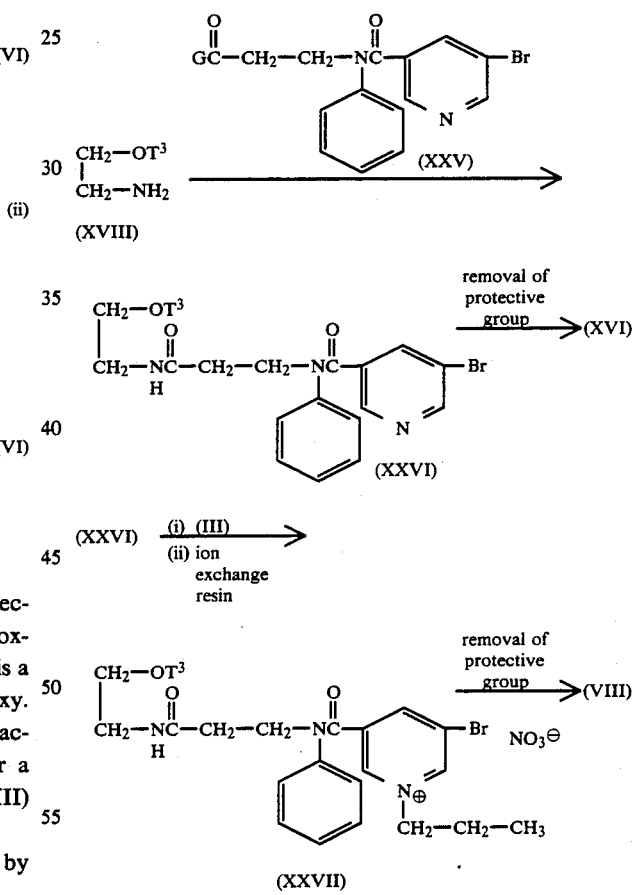

wherein $T^3$ is a protective group (a hydroxy-protective group such as diphenylmethyl, trifluoroacetyl, 2-tetrahydropyranyl, trityl, or benzyl) and G is the same as described above.

The reaction between the compounds (XXIV) and (XXV) is performed under the same condition as that for the reaction between the compounds (VIII) and (Ix) by Method D, and the reaction between the compounds (XXVI) and (III) is performed under the same condition as that for the reaction between the compounds (II) and (III by Method A.

The compounds (X) and (XVII) can be obtained for example by the following method.

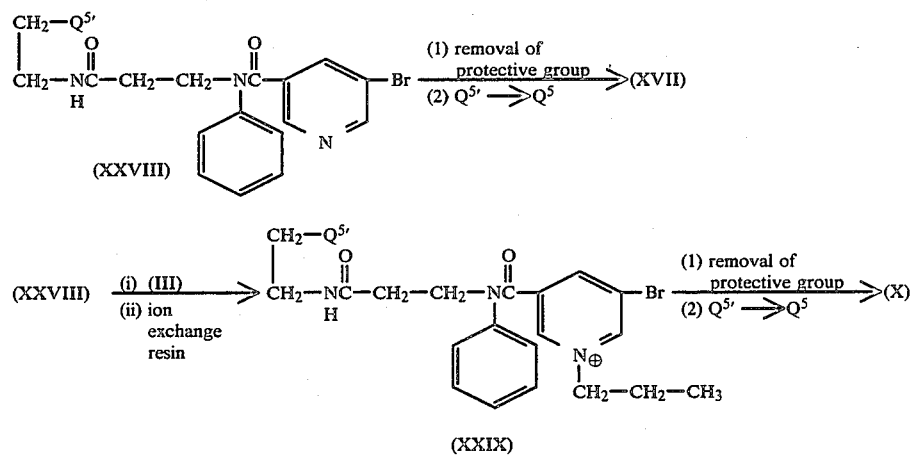

wherein $Q^{5'}$ is a protected hydroxyl (e.g. diphenylmethyloxy, trifluoroacetoxy, 2-tetrahydropyranyloxy, trityloxy, benzyloxy).

The reaction between the compounds (XXVIII) and (III) is performed under the same condition as that for the reaction between the compounds (II) and (III) by Method A described above.

The reaction $Q^{5'} \rightarrow Q^5$ is performed by the following method after removal of the protective group. (i) When $Q^{5'} =$

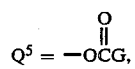

$$Q^5 = -O\overset{O}{\underset{\|}{C}}G,$$

the compound after removal of the protective group is allowed to react with a compound (XXVIII) or (XXIX) of which $Q^{5'}$ is —OH and a carbonyl halide such as phosgene.

All of these reactions are known per se and can be performed under respective conditions.

Removal of the protective group described above can be performed by a per se known method. Namely, benzyl and diphenylmethyl can be removed by a catalytic reduction in the presence of a catalyst (palladium carbon, platinum oxide, etc.) in a solvent (e.g. alcohol, acetic acid, water tetrahydrofuran, or a mixture thereof) (reaction temperature, room temperature to $+100°$ C.).

Trityl and 2-tetrahydropyranyl can be removed in a solvent (e.g. water, alcohol, tetrahydrofuran, dioxane, etc.) in the presence of an acid (e.g. mineral acids such as hydrochloric acid, phosphoric acid, sulfuric acid, and organic acids such as toluenesulfonic acid, methanesulfonic acid, acetic acid) at $0°$ C. to $+150°$ C. Trifluoroacetyl can be removed readily by treatment with an alkali (e.g. aqueous solution of sodium hydroxide or sodium hydrogencarbonate).

Separation from the reaction mixture and purification of the compound (I) is performed by the routine methods for separation and purification (e.g. extraction, concentration, filtration, recrystallization, column chromatography, thin layer chromatography).

Compound (I), being an excellent PAF-antagonist, is useful as a preventive and therapeutic drug for treatment of circulatory diseases caused by PAF, such as thrombosis, cerebral apoplexy (e.g. cerebral hemorrhage, cerebral thrombosis), myocardial infarction, angina pectoris, thrombotic phlebitis, nephritis (e.g. glomerular nephritis), diabetic nephrosis, shock (e.g. endotoxin shock observed after severe infection or postoperatively, intravascular agglutination syndrome caused by endotoxin, anaphylactic shock, hemorrhagic shock); digestive tract diseases caused by PAF (e.g. gastric ulcer); diseases related to allergy and inflammation (e.g. tracheal asthma, psoriasis); pneumonia; rejection due to increased PAF production after implantation of organs; and postoperative organodysfunction (e.g. in heart, liver, kidney). It can also be used for suppression of contraception of female mammals by suppressing cell division and/or implantation on the uterus.

The compound (I) can also be administered as an effective agent for prevention or treatment of hyperendothelinemia induced by excess secretion of endothelin [Nature, 332, 411 (1988)] which is known to have potent activities on contraction of vascular and bronchial smooth muscle and to induce hypertension and bronchoconstriction. In a higher concentration (about 0.1 to 5 nmol per 100 ml of blood), endothelin also induces various diseases such as ischemic cerebropathies and cardiopathies (e.g. cerebral apoplexy, angina pectoris, myocardial infarction, heart failure, arrhythmia), renal disorders (e.g. renal inflammation), circulatory disorders of various organs (e.g. liver, lung, intestine) and asthma and causes death in animal individuals in some cases.

Because the compound (I) has a low toxicity, it can be administered orally or parenterally to mammals (e.g. human, rabbit, dog, cat, rat, mouse, guinea pig) as powders or as pharmaceutical compositions in appropriate drug forms. The dose varies according to the subjects and diseases to be treated, symptoms, route of administration, etc.; for example for prevention and treatment of shock in adults, it is desirable that the compound (I) is given usually at the unit dose of 0.001 to 1.0 mg/kg body weight, desirably at 0.01 to 0.1 mg/kg body weight, once to 5 times a day, desirably once to three times a day, by intravenous injection. The compound (I) can be given by drip infusion at the unit dose of 0.01 to 0.1 mg/kg body weight/min. over about one hour, once to 5 times a day, desirably once to three times a day. Parenteral or oral administration for other purposes can be performed at a similar dose to those described above. When the shock symptoms are very severe, the dose may be increased according to the severity.

For oral administration for prevention and treatment of diseases such as thrombosis, asthma, and nephritis in adults, it is desirable that the compound (I) is given usually at the unit dose of 0.1 to 30 mg/kg body weight, preferably at 1 to 10 mg/kg body weight, once to 5 times a day, preferably once to three times a day. For parenteral administration for other purposes the compound can be given at a similar dose as that described above.

Pharmaceutical compositions used for administration contain an effective dose of the compound (I) and a pharmaceutically acceptable carrier or excipient and are prepared in drug forms appropriate for oral or parenteral administration.

Compositions for oral administration include solid or liquid drug forms, and to be concrete, tablets (sugar coated tablets, film coated tablets), pills, granules, powders, capsules (including soft capsules), syrups, emulsions, and suspensions. These compositions are produced by the per se known methods and contain carriers or excipients usually used for pharmaceutical preparations. Such carriers and excipients include lactose,, starch, sucrose, and magnesium stearate. Composition for parenteral administration include injections, suppositories, ointments, fomentations, and paints. Injections include those for intravenous, subcutaneous, intradermal, intramuscular administration and drip infusion. These injections are prepared by the per se known methods, for example, by dissolving, suspending, or emulsifying the compound (I) in a sterile aqueous or oily liquid used usually for injection use. Aqueous solutions for injection use include physiological saline, and isotonic solutions containing glucose and other supplemental drugs, and may be combined with appropriate solubilizing agents such as alcohol (e.g. ethanol), polyalcohol (e.g. propylene glycol, polyethyleneglycol), and non-ionic surfactants [e.g. Polysorbate 80, HCO-50 (polyoxyethylene (50 mol) adduct of hydrogenated castor oil)]. Oily liquids include sesame oil and soybean oil, and may be combined with benzyl benzoate or benzyl alcohol as a solubilizing agent. Injections prepared are usually filled in appropriate ampoules and offered as injections. Suppositories for rectal administration are prepared by the per se known methods, for example by mixing the compound (I) with a base usually used for suppositories, followed by molding.

The composition may contain other active substances as far as they do not give rise to undesirable interaction due to combination with the compound (I). For example, for mammals with infection, the compound (I) can be given with an antibiotic for prevention of endotoxin shock.

Pyridinium nitrate (I) of this invention has an excellent PAF-antagonism even after oral administration. Therefore pyridinium nitrate (I) can be given not only parenterally by injection but also orally. Pyridinium nitrate (I) of this invention is more stable than the corresponding chloride and thus used advantageously as drugs.

EXAMPLE

The following examples will explain the effect of this invention in more detail.

Example 1

Inhibition of platelet aggregation

[Test method]

Blood was drawn from a male rabbit directly by cardiopuncture with a syringe containing 3.15% citric acid as an anticoagulant (one volume to 9 volumes of blood). By centrifugation at 800 rpm for 10 minutes at room temperature, platelet rich plasma (PRP) was obtained. The residual blood was centrifuged again at 3000 rpm for 10 minutes to give platelet poor plasma (PPP) as the supernatant. PRP was diluted with PPP so that the platelet count might be adjusted to about 500,000 cells/$\mu$l. 250 $\mu$l of this PRP was stirred at 37° C. for 2 minutes, and the test substance [the compound (6) obtained in Production Example 1] was added. The mixture was stirred again for 2 minutes, followed by the addition of PAF of a certain concentration. Platelet aggregation was measured with a platelet aggregometer (manufactured by Rika Denki Co. in Japan). The aggregation inhibition by the test substance was determined as the percentage of reduction from the maximal transmittance (the maximal aggregation) by PAF in the control PRP.

The results are summarized in Table 1.

TABLE 1

| Inhibitory action on PAF-induced rabbit platelet aggregation | | |
|---|---|---|
| Concentration of test substance and rate of inhibition (%) | | |
| $3 \times 10^{-8}$ M | $3 \times 10^{-7}$ M | $3 \times 10^{-6}$ M |
| 71 | 100 | 100 |

Example 2

Inhibitory action on PAF-induced hypotension in rats

[Test Method]

Male Sprague-Dawley rats weighing about 250 g were used. Cannulas were inserted into the unilateral femoral artery for measurement of blood pressure and into the unilateral femoral vein for administration of the drug solution. Blood pressure was measured via a pressure transducer and recorded on a polygraph. Blood pressure decrease was measured after intravenous (i.v.) injection of PAF at 1 $\mu$g/kg, and then the test substance [the compound (6) in Production Example 1] was given intravenously or orally; PAF at 1 $\mu$g/kg was given intravenously 5 minutes and 1, 2, 4, 6, and 8 hours after the intravenous injection, and 1, 2, 4, 6 and 8 hours after the oral administration, and the blood pressure decrease was measured.

[Results]

The inhibitory action on PAF-induced hypotension was expressed in the ratio of decrement of blood pressure due to PAF before the treatment with the test substance (mmHg) to the decrement after the treatment with the test substance (mmHg). The results are summarized in Table 2 and in Table 3.

TABLE 2

| dose mg/kg | Inhibition of hypotensive effect (i.v. administration) inhibition (%) | | | | | |
|---|---|---|---|---|---|---|
| | 5 minutes | 1 hour | 2 hour | 4 hour | 6 hour | 8 hour |
| 0.01 | 93 | 84 | 68 | 48 | 44 | 24 |

TABLE 3

| dose mg/kg | Inhibition of hypotensive effect (p.o. administration) inhibition (%) | | | | |
|---|---|---|---|---|---|
| | 1 hour | 2 hour | 4 hour | 6 hour | 8 hour |
| 1 | 69 | 87 | 82 | 76 | 69 |

Example 3

Reversed passive Arthus reaction in rat

[Test method]

Hair was removed at the back of a male Sprague-Dawley rat (7-week-old, weighing about 250 g) under slight anesthesia with ether and a solution of the test substance [the compound (6) obtained in the Production Example 1] in physiological saline was injected into the caudal vein at the dose of 0.2 ml per 100 g of body weight. Immediately 1 ml of 0.5% antigenic egg albumin solution in physiological saline was injected into the caudal vein. Immediately 0.1 ml of the rabbit anti-egg albumin antiserum (containing 6 mg protein antibody/ml) was given subcutaneously at a site each on the right and the left side of the back. Three hours later, 1 ml of 1% Evans Blue solution in physiological saline was injected intravenously, the skin was removed after 30 minutes, and the area stained blue was measured (in mm²). The extent of inhibition was calculated by comparing the area with that in the group without treatment with the test substance.

[Results]

The compound (6) produced in the Production Example 1 showed inhibition when given intravenously in the Test, the $ID_{50}$ value being 1.2 $\mu g/kg$.

Example 4

Inhibition of PAF in tracheal obstruction

Male and female Hartley guinea pigs weighing about 400 g each were used. The animal was fixed in the supine position under anesthesia with urethane (1.5 g/kg, i.p.), one of the 4 branches of a cannula was inserted into the trachea, and two of the other 3 branches were connected to a respirator (Harvard apparatus rodent respirator). The last branch was connected to a bronchospasm transducer 7020 (Ugobasile). Air was pumped into the lung at the rate of 5 to 7 ml at a time and 70 times per minutes at the loading pressure to the lung of 10 cm $H_2O$, and the volume of the overflown air was recorded via a transducer on the Rectigraph (Rectigraph-8S, San-ei Sokki). After treatment with gallamine triethodide (1 mg/kg, i.v.), histamine dihydrochloride (10 $\mu g/kg$) was intravenously injected, and the responsiveness of the animal was investigated. Thirty seconds after intravenous injection of PAF (0.3 $\mu g/kg$), a maximal airway constriction was observed. Under the conditions, the test substance [the compound (6) obtained in the Production Example 1] was examined for its inhibitory action. The test substance was dissolved in physiological saline, and given intravenously two minutes before PAF administration. The compound (6) of the Production Example 1, when given intravenously at the dose of 0.03 mg/kg, inhibited the PAF-induced airway constriction by 91.3%.

Example 5

Acute toxicity

Male J cl-ICR mice (5 animals) (aged 5 weeks) were used. The compound (6) obtained in the Production Example 1 was given to the animals orally at the dose of 1000 mg/kg or intravenously at the dose of 10 mg/kg; no death was observed until one week later.

Example 6

Stability test

The compounds obtained were examined for their stability in the form of powders. Test substance: the compound (6) from the Production Example 1. The compound (7) from the Reference Example 1 was used as the control compound. Procedure: About 100 mg each of the test substance was placed into glass bottles, which were then closed tightly and kept at room temperature (20±2° C.) and at 40° C. (not for the control compound) for 30 days. Determination of the content: An aliquot of the test substance was dissloved in the mobile phase for high performance liquid chromatography [acetonitrile:methanol:0.1% phosphoric acid=900:240:2100] and the content was determined by HPLC.

Conditions of HPLC: column YMC ODS A302 4.6×150 mm flow rate 0.7 ml/min.

detection UV 254 nm

Results: Remaining percentages of the test substance after 30 days of storage are shown in Table 4.

TABLE 4

| Test substance | remaining percentage (%) | |
|---|---|---|
| | at room temperature | at 40#C |
| Compound (6) of Production Example 1 | 100.2 | 99.3 |
| Control compound (Compound (7)) | 65.0 | not examined |

Example 7

Effect on endotoxic shock (1) Reversal of endotoxin (ET)-induced hypotension in rats Method: Male SD rats were anesthetized with sodium pentobarbital, and the right femoral artery and left femoral vein were cannulated for blood pressure measurement and for injection of the compound (6) obtained in the Production Example 1 or ET (*E. Coli*, 0111, B4), respectively. The compound (6) obtained in the Production Example 1 was given eight minutes after the injection of ET (15 mg/kg).

Result: ET gradually reduced blood pressure and a nadir was reached about 8 minutes after the injection, thereafter the pressure recovered slowly. The compound (6) obtained in the Production Example 1 potently and rapidly reversed the ET-induced hypotension with an $ED_{50}$ value of 1.2 $\mu g/kg$.

(2) Inhibition of endotoxin (ET)—induced death in rats

Method: Male SD rats were used. ET (E. Coli, 0111, B4) (15 mg/kg) was given i.v. 5 min after the injection of the compound (6) obtained in the Production Example 1. Survival rate was observed for 1 week.

Result: The compound (6) obtained in the Production Example 1 at a dose of 100 μg/kg significantly improved the survival rate of rats for almost 1 week (Table 4).

TABLE 4

Protective action against ET-iduced death in rats

| | Dose lg/kg,i.v. | No. of rats | Survival rate (%) (Survived rats/Used rats) 22 hr | 6 day |
|---|---|---|---|---|
| Control | — | 10 | 1/10 (10%) | 0/10 (0%) |
| Compound (6) of Production Example 1 | 10 | 10 | 3/10 (30%) | 3/10 (30%) |
| | 100 | 10 | 6/10 (60%)* | 4/10 (40%)* |

*$P<0.05$ vs control (by $X^2$-test)

Example 8

Inhibition of experimental disseminated intravascular coagulation (DIC) in rats

Method: Male SD rats were anesthetized with sodium pentobarbital. Endotoxin (E. Coli, 0111, B4) (ET) was infused into the right femoral vein at a rate of 250 μg/kg/hr for 4 hr. The compound (6) obtained in the Production Example 1 (Test compound) at a dose of 200 μg/kg was given i.v. bolus 5 min. before the infusion of ET and was then infused at a rate of 200 μg/kg/hr for 4 hr.

Result: The infusion of ET caused disseminated intravascular coagulation (DIC) symptoms: a reduction in platelet counts, significant changes in parameters for coagulation (prothrombin time (PT): activated partial thromboplastin time (APTT) and fibrinogen level) and fibrinolysis (FDP level) (Table 5). The compound (6) obtained in the Production Example 1 significantly inhibited the changes in these DIC parameters.

obtained in the Production Example 1 was given i.v. 5. min. before the rechallenge with BSA.

Result: Pretreatment with the compound (6) obtained in the Production Example 1 protected mice from anaphylactic shock with an $ED_{50}$ value of 2.6 μg/kg.

Experiment 10

Effect on acute renal failure in rats

Method: Male Sprague Dawley (Jcl) rats, 5 weeks old, were anesthetized with sodium pentobarbital (50 mg/kg, i.p.) and the renal artery was occluded bilaterally for 45 minutes followed by reperfusion for 20 hours. The blood was collected from the abdominal aorta under anesthesia for measurement of blood urea nitrogen (BUN).

Results: The concentration of BUN was markedly elevated 20 hours after reperfusion. The compound (6) obtained in the Production Example 1 at an oral dose of 30 mg/kg, which was given 1 hour prior to the occlusion of renal artery, inhibited significantly the elevation of BUN (Table 6).

TABLE 6

Effect on acute renal failure in rats

| | No. of animal | Blood urea nitrogen (BUN) (mg/dl) |
|---|---|---|
| Control | 10 | 110 ± 4 |
| Compound (6) of Production Example 1 | 3 | 88 ± 2* |

Student's t-test, *$P<0.05$

Preparation Example 1

3-bromo-5-[N-phenyl-N-[2-[[2-(1,2,3,4-tetrahydro-2-isoquinolylcarbonyloxy)ethyl]carbamoyl]ethyl]carbamoyl]-1-propylpyridinium nitrate (10 g) is dissolved in distilled water (1.0 ml). After sterile filtration for sterilization, the solution is distributed into 1000 vials by 1 ml portions and lyophilized, followed by tightly closing.

On the other hand, distilled water (2 ml) for injection containing mannitol (100 g) is distributed into 1000 ampoules for injection by 2 ml portions, followed by

TABLE 5

Inhibitory effect on disseminated intravascular coagulation (DIC) in rats.

| Group | No. of rats | Platelets ($\times 10^4/\mu l$) | PT (sec) | APTT (sec) | Fybrinogen (mg/ml plasma) | FDP (μg/ml plasma) |
|---|---|---|---|---|---|---|
| Normal (0.9% saline (0.6 ml/hr) was infused for 4 hr) | 7 | 71 ± 3 | 11.2 ± 0.2 | 35.3 ± 1.3 | 2.7 ± 0.1 | 0.5 ± 0.0 |
| Control (Endotoxin (0.25 mg/kg/hr) was infused for 4 hr) | 14 | 23 ± 3 | 18.9 ± 1.3 | 58.3 ± 3.6 | 0.3 ± 0.1 | 16.8 ± 2.3 |
| Test compound (Test compound (200 μg/kg) was given before ET and infused (200 μg/kg/hr) for 4 hr) | 14 | 40 ± 4** | 14.0 ± 0.4** | 42.8 ± 1.5** | 1.2 ± 0.3** | 4.6 ± 0.8** |

**$P<0.01$ vs control (by Williams-Wilcoxon test)

Example 9

Protective effect against death induced by anaphylactic shock in mice

Method: Male mice were sensitized with bovine serum albumin (BSA) and killed Bordetella pertussis. Two to three weeks later, the mice were rechallenged with BSA (1 mg/kg, i.v.). Survival rate was determined 60 min after the injection of BSA. The compound (6)

sealing to prepare 1000 injectable solutions.

On the occasion of use, the powder in the former vial is dissolved in the mannitol solution for injection.

Preparation Example 2

3-bromo-5-[N-phenyl-N-[2-[[2-(1,2,3,4-tetrahydro-2-isoquinolylcarbonyloxy)ethyl]carbamoyl]ethyl]carbamoyl]-1-propylpyridinium nitrate (10 g), lactose (90 g) and corn starch (17 g) are mixed, and granulated with a paste prepared with corn starch (7 g). The granules are incorporated with corn starch (5 g) and magnesium stearate (1 g) and compressed to prepare 1000 tablets.

Production Example 1

3-bromo-5-[N-phenyl-N-[2-[[2-(1,2,3,4-tetrahydro-2isoquinolylcarbonyloxy)ethyl]carbamoyl]ethyl]carbamoyl]-1-propylpyridinium nitrate (6)

(i) Synthesis of
1-t-butoxycarbonylamino-2-(1,2,3,4-tetrahydro-2-isoquinolylcarbonyloxy)ethane (1)

1.222 g (20 mmole) of monoethanolamine was dissolved in 40 ml of methylene chloride, to which 4.365 g (20 mmole) of di-t-butyl dicarbonate was added with ice-cooling, and stirred at room temperature for 2 hours.

To the reaction mixture 3.235 ml (40 mmole) of pyridine was added, and then 2.51 ml (20 mmole) of phenylchlorocarbonate was added with ice-cooling, and the mixture was stirred at room temperature for 10 minutes. The reaction mixture was washed with a 5% sodium hydrogencarbonate aqueous solution, and the organic phase was dried with anhydrous sodium sulfate, followed by evaporation of the solvent under reduced pressure, to give a crude carbonate derivative.

To the crude carbonate derivative 2.75 ml (22 mmole) of 1,2,3,4-tetrahydroisoquinoline was added and it was heated at 90° C for one hour. The crude product obtained after cooling was purified by column chromatography (silica gel: 200 g; eluant: hexane/ethyl acetate =2/1-1/1), to give 5.757 g of the desired substance (1) (89.7%, white solid).

TLC (Silica Gel; n-hexane/AcOEt=1/1): Rf=0.22
NMR (90 MHz, CDCl$_3$) δ: 1.43 (9H, s), 2.83 (2H, t), 3.40 (2H, q), 3.67 (2H, t), 4.18 (2H, t), 4.60 (2H, s), 5.00 (1H, br), 7.14 (4H, s).
IR (Kbr) cm$^{-1}$: 3340, 2970, 1710, 1670, 1520, 1478, 1430, 1365, 1290, 1230

(ii) Synthesis of
2-(1,2,3,4-tetrahydro-2-isoquinolylcarbonyloxy)ethylamine (2)

5.435 g (16.9 mmole) of the compound (1) synthesized in (i) was dissolved in 15 ml of chloroform, to which 10 ml of hydrochloric acid-saturated methanol was added, and the mixture was stirred at room temperature for 2 hours. The reaction mixture was concentrated under reduced pressure, and 50 ml of 1 N sodium hydroxide aqueous solution was added to the resultant crude product, followed by extraction with chloroform. The organic phase was dried with anhydrous potassium carbonate, and the solvent was evaporated off under reduced pressure, to give 3.72 g of the desired compound (2) (100%, colorless oil).

TLC (Silica Gel; MeOH/conc. NH$_4$OH=50/1): Rf=0.37
NMR (90 MHz, CDCl$_3$) δ: 1.36 (2H, s), 2.84 (2H, t) 2.95 (2H, t), 3.69 (2H, t), 4.16 (2H, t), 4.63 (2H, s), 7.17 (4H, s).
IR (Neat) cm$^{-1}$: 3360, 2940, 1690, 1580, 1430, 1295, 1230, 1120.

(iii) Synthesis of
N-[2-(1,2,3,4-tetrahydro-2-isoquinolylcarbonyloxy)ethyl]-3-[(N'-t-butoxycarbonyl-N'-phenyl)-amino]propanamide (3) 3.714 g (14.0 mmole) of 3-(N-t-butoxycarbonyl-N-phenyl)aminopropionic acid and 3.177 g (15.4 mmole) of dicyclohexylcarbodiimide were dissolved in 50 ml of methylene chloride, to which 3.084 g (14.0 mmole) of the compound (2) synthesized in ii) was added with ice-cooling, and the mixture was stirred at room temperature for 4 hours. The precipitate was filtrated off, and the mother liquor was washed with 1 N NaOH aqueous solution, followed by drying of the organic phase with anhydrous potassium carbonate and evaporation of the solvent under reduced pressure. The resultant crude product was purified by column chromatography (silica gel: 200 g; eluant: hexane/ethyl acetate=3/7), to give 5.00 g of the desired substance (3) (76.4%, colorless syrup).

TLC (Silica Gel; hexane/AcOEt=½): Rf=0.24
NMR (90 MHz, CDCl$_3$) δ: 1.39 (9H, s), 2.47 (2H, t), 2.84 (2H, t), 3.49 (2H, q), 3.69 (2H, t), 3.93 (2H, t), 4.20 (2H, t), 4.62 (2H, s), 6.59 (1H, br), 7.0–7.5 (9H, m)
IR (Neat) cm$^{-1}$: 3320, 2980, 2930, 1710–1650, 1598, 1540, 1498, 1455, 1430, 1390, 1364, 1300, 1230, 1160.

(iv) Synthesis of
N-[2-(1,2,3,4-tetrahydro-2-isoquinolylcarbonyloxy)ethyl]-3-anilinopropanamide (4) 4.675 g (10.0 mmole) of the compound (3) synthesized in (iii) was dissolved in 10 ml of chloroform and 10 ml of methanol, to which 20 ml of hydrochloric acid-saturated methanol was added, and the mixture was stirred at room temperature for 3 hours. The reaction mixture was concentrated under reduced pressure, to which 50 ml of 1 N sodium hydroxide aqueous solution was added, followed by extraction with chloroform. The organic phase was dried with anhydrous potassium carbonate, the solvent was evaporated off under reduced pressure, and the resultant crude product was purified by column chromatography (silica gel: 80 g; eluant: hexane/ethyl acetate=1/6-1/8), to give 3.158 g of the desired compound (4) (85.9%, white solid).

TLC (Silica Gel; hexane/AcOEt=1/6): Rf=0.28
NMR (90 MHz, CDCl:) δ: 2.45 (2H, t), 2.80 (2H, t), 3.3–3.8 (6H, m), 4.22 (2H, t), 4.56 (2H, s), 6.43, (1H, br), 6.66 (3H, m), 6.9–7.3 (6H, s).
IR (KBr) cm$^{-1}$: 3310, 1690, 1660, 1560, 1640, 1443, 1430, 1299, 1282, 1240, 1230, 1130, 1115, 1095.

(v) Synthesis of
3-bromo-5-[N-phenyl-N-[2-[[2-(1,2,3,4-tetrahydro-2-isoquinolylcarbonyloxy)ethyl]carbamoyl]ethyl]carbamoyl]pyridine (5)

735 mg (2 mmole) of the compound (4) synthesized in iv) and 1.394 ml (10 mmole) of triethylamine were dissolved in 15 ml of chloroform, to which 617 mg (2.4 mmole) of 5-bromonicotinoyl chloride hydrochloride was added with ice-cooling, and the mixture was stirred at room temperature for 1.5 hours. To the reaction mixture 1 N NaOH aqueous solution was added, followed by extraction with chloroform, drying of the organic phase with anhydrous potassium carbonate, and evaporation of the solvent under reduced pressure. The resultant crude product was purified by column chromatography (silica gel: 30 g; eluant: ethyl acetate), to give 1.083 g of the desired compound (5) (98.2%, white powder).

TLC (Silica Gel; AcOEt): Rf=0.26

NMR (90 MHz, CDCl:) δ: 2.58 (2H, t), 2.81 (2H, t), 3.51 (2H, q), 3.65 (2H, t), 4.20 (4H, m) 4.58 (2H, s), 6.79 (1H, br t), 6.9–7.4 (9H, m), 7.77 (1H, t), 8.29 (1H, br s), 8.47 (1H, br s).

IR (Neat) cm$^{-1}$: 3320, 1710–1620, 1595, 1540, 1490, 1440, 1390, 1340, 1295, 1230, 1120, 1095.

(vi) Synthesis of 3-bromo-5-[N-phenyl-N-[2-[[2-(1,2,3,4-tetrahydro-2isoquinolylcarbonyloxy)ethyl]carbamoyl]ethyl]carbamoyl]-1-propylpyridinium nitrate (6)

To 1.53 g (2.77 mmole) of the compound (5) synthesized in (v), 50 ml of 1-iodopropane was added, followed by refluxing by heating under air flow and by shielding from light for 4 hours. After cooling, the mixture was concentrated under reduced pressure, and the resultant crude product was dissolved in 70 ml of 70% methanol/water, treated with IRA-410 (NO$_3^-$) [70 ml], and purified by column chromatography (silica gel; eluant: chloroform/ methanol=5/1), to give 1.34 g of the desired compound (6)(73.6%, light yellow powder).

NMR (200 MHz, CDCl$_3$) δ: 0.76 (3H, t, J=7 Hz), 1.82 (2H, m), 2.67 (2H, m), 2.83 (2H, t, J=6 Hz), 3.45 (2H, q, J=5 Hz), 3.66 (2H, t, J=6 Hz), 4.15 (2H, t, J=6 Hz), 4.18 (2H, t, J=6 Hz), 4.00 (2H, s), 4.65 (2H, t, J=7 Hz), 6.90–7.40 (9H, m), 7.72 (1H, m), 8.24 (1H, br s}, 9.03 (1H, br s), 9.32 (1H, br s).

IR (KBr) cm$^{-1}$:3420, 3050, 1680, 1660, 1590.

Reference Example 1

3-Bromo-5-[N-phenyl-N-[2-[[2-(1,2,3,4-tetrahydro-2-isoquinolylcarbonyloxy)ethyl]carbamoyl]ethyl]carbamoyl]-1-propylpyridinium chloride (7)

To 827 mg (1.50 mmole) of the compound (5) synthesized in Production Example 1-v) 25 ml of 1-iodopropane was added and refluxed by heating for 68 hours under air flow and by shielding from light. After cooling the reaction mixture was concentrated under reduced pressure, the resultant product was dissolved in 70 ml of 70% methanol/water, treated with IRA-410 (Cl$^-$) [70 ml], and purified by column chromatography (silica gel: 35 g; eluant: chloroform/methanol=6/1), to give 691 mg of the desired compound (7) (73.1%, light yellow powder).

TLC (Silica Gel; CHCl$_3$/MeOH=6/1): Rf=0.30

NMR (90 MHz, CDCl$_3$) δ: 0.76 (3H, t), 1.85 (2H, m), 2.81 (4H, m), 3.43 (2H, m), 3,65 (2H, t), 4.15 (4H, m), 4.58 (2H, s), 4.85 (2H, m), 7.0–7.5 (9H, m), 8.09 (1H, m), 8.35 (1H, br s), 9.60 (2H, br s).

IR (KBr) cm$^{-1}$: 3380, 3200, 2960, 1690, 1658, 1595, 1550, 1495, 1430, 1298, 1228, 1120, 745.

What is claimed is:

1. A compound of the formula:

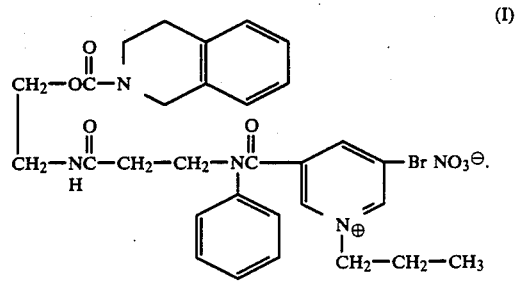

2. A pharmaceutical composition suitable for inhibiting activities of platelet activating factor which comprises
    (a) as the active ingredient, an amount effective to inhibit activities of platelet activating factor of a compound as claimed in claim 1
    (b) a pharmaceutically acceptable carrier or excipient therefor.

3. A method for inhibiting activities of platelet activating factor in a mammal, which comprises administering to said mammal an amount effective to inhibit activities of platelet activating factor of a compound as claimed in claim 1.

* * * * *